United States Patent [19]

Huber

[11] 4,180,559
[45] Dec. 25, 1979

[54] COATED 1-(2-CHLORODIBENZO[b,f]OXEPIN-10-YL)-4-METHYLPIPERAZINE COMPOSITIONS

[75] Inventor: Harold E. Huber, Cincinnati, Ohio

[73] Assignee: Richardson-Merrell Inc., Wilton, Conn.

[21] Appl. No.: 964,008

[22] Filed: Dec. 1, 1978

Related U.S. Application Data

[63] Continuation-in-part of Ser. No. 867,167, Jan. 5, 1978, abandoned.

[51] Int. Cl.² ............................................. A61K 9/36
[52] U.S. Cl. .................................................. 424/35
[58] Field of Search ........................................ 424/35

[56] References Cited

U.S. PATENT DOCUMENTS

| | | | |
|---|---|---|---|
| 3,681,354 | 8/1972 | Mastursi et al. | 260/268 X |
| 4,001,390 | 1/1977 | Ohno et al. | 424/35 |
| 4,017,647 | 4/1977 | Ohno et al. | 424/35 |

*Primary Examiner*—Shep K. Rose
*Attorney, Agent, or Firm*—William J. Stein; Eugene O. Retter; George W. Rauchfuss, Jr.

[57] ABSTRACT

A coated 1-(2-chlorodibenzo[b,f]oxepin-10-yl)-4-methylpiperazine composition, suitable for pharmaceutical use.

5 Claims, No Drawings

COATED 1-(2-CHLORODIBENZO[b,f]OXEPIN-10-YL)-4-METHYLPIPERAZINE COMPOSITIONS

CROSS REFERENCE TO RELATED APPLICATIONS

This application is a continuation-in-part of application Ser. No. 867,167, filed Jan. 5, 1978, now abandoned.

BACKGROUND OF THE INVENTION

U.S. Pat. No. 3,681,354 discloses a class of dibenzo[b,f]oxepin-10-yl derivatives stated to have useful pharmacological properties including hypertensive, sedative, muscle relaxant, local anesthetic, analgesic, antipyretic and anti-inflammatory properties. The present invention is directed to certain coated pharmaceutical compositions containing the compound 1-(2-chlorodibenzo[b,f]oxepin-10-yl)-4-methylpiperazine described generically therein. This compound is a useful psychotropic agent and possesses particularly useful antipsychotic properties. The coated pharmaceutical compositions described herein are of particular value in providing therapeutically effective blood levels of this drug.

Prior to the present invention, the usefulness of this drug has been limited due to its degradation at low pH levels in the stomach, resulting in a poor and erratic absorption into the bloodstream. The compound 1-(2-chlorodibenzo[b,f]oxepin-10-yl)-4-methylpiperazine belongs to a class of enamines which is known to readily undergo hydrolytic cleavage in an aqueous acidic medium. Unfortunately, the compound 1-(2-chlorodibenzo[b,f]oxepin-10-yl)-4-methylpiperazine is no exception and possesses a high degree of acid lability under aqueous conditions resulting in the formation of the compound 2-chloro-dibenzo[b,f]oxepin-10-one as indicated below.

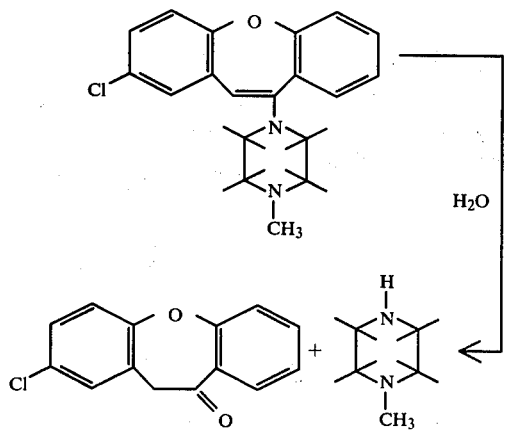

Under the normal conditions of gastric acidity, the pharmaceutically active compound undergoes hydrolytic cleavage with a concomitant loss of activity. It is well documented that the pH of the stomach contents can vary from 1.5 to 4 and that gastric residual time can range from less than 1 hour to 4 or more hours. Thus, the amount of undestroyed drug available at the site of absorption varies erratically from patient to patient depending upon such factors as amount and type of food intake, food composition and the rate of gastric emptying at the time of drug administration. Furthermore, the problem of absorbing the therapeutically active compound into the blood stream is compounded by the fact that this particular compound is soluble in aqueous solutions of low pH, precisely where the compound is most labile, whereas in aqueous solutions that have a pH greater than 7.5, the compound is insoluble.

The concept of using enteric coatings to protect drugs that are destroyed in gastric fluids is, of course, well known. Shellac and cellulose acetate phthalate meet most of the criteria of a good enteric coating and they are among the most widely used coating materials for this purpose. These coatings are generally designed to pass the drug intact or in concentrated form through the stomach, and to deliver the drug to the more alkaline sites of absorption in the small and lower intestine. Unfortunately, such enteric coatings are unsuitable for use with the compound 1-(2-chlorodibenzo[b,f]oxepin-10-yl)-4-methylpiperazine, inasmuch as they deliver the therapeutic agent to alkaline absorption sites where the compound is insoluble and poorly absorbed.

U.S. Pat. No. 4,001,390 discloses the use of hydroxypropyl methylcellulose phthalate coatings on solid dosage forms in combination with dyes and/or pigments so as to provide thin coating layers having a sufficient hiding power and providing a glossy and elegant finish. Such results are achieved by means of three successive coating layers, an undercoat containing the polymeric coating material, a secondary coat composed of the polymeric coating substance and a pigment, and a finish coat composed of the polymeric coating material. In contrast thereto the instant invention utilizes a single coating having a critical thickness of certain hydroxypropyl methylcellulose phthalate polymers to prepare duodenal soluble pharmaceutical compositions containing 1-(2-chlorodibenzo[b,f]oxepin-10-yl)-4-methylpiperazine suitable for oral administration. The coatings described herein are of such a nature as to protect the compound 1-(2-chlorodibenzo[b,f]oxepin-10-yl)-4-methylpiperazine from acid degradation in strongly acidic gastric fluids, but are designed to dissolve at the weakly acidic pH of 5.0 to 5.5 in order to permit dissolution and absorption of the drug substance.

U.S. Pat. No. 4,017,647 relates to the preparation of enteric coated dosage forms using an aqueous alkaline solution of certain polymeric substances including hydroxypropyl methylcellulose phthalate. Subsequent treatment of these coated dosage forms converts these polymeric coatings to a water-insoluble form stated to be suitable as enteric coatings. Such coatings, however, are ineffective for use with the particular therapeutic agent to which the invention relates due to the acid instability and the insolubility in neutral or alkaline aqueous solutions of the active ingredient.

I have discovered that the controlled use of a particular enteric coating material, viz, hydroxypropyl methylcellulose phthalate, results in the preparation of a duodenal-soluble coating which will sufficiently protect the compound 1-(2-chlorodibenzo[b,f]oxepin-10-yl)-4-methylpiperazine from acid degradation in gastric fluids, and yet will permit sufficient absorption of the compound to take place in the duodenum so as to be therapeutically useful. More particularly, I have discovered that these hydroxypropyl methylcellulose phthalate coatings dissolve at a pH of about 5.0 to 5.5, and when present at a coating thickness of about 0.1 mm to 0.2 mm, release the compound under the slightly acidic conditions of the duodenum, where the compound is sufficiently stable and yet sufficiently soluble so as to be available for absorption into the bloodstream of the treated patient.

SUMMARY OF THE INVENTION

This invention relates to novel duodenal-soluble coated pharmaceutical compositions for the compound 1-(2-chlorodibenzo[b,f]oxepin-10-yl)-4-methylpiperazine and its pharmaceutically acceptable salts. More particularly, this invention relates to duodenal-soluble coated compositions suitable for oral ingestion comprising a core having from about 6 to about 33% by weight of 1-(2-chlorodibenzo[b,f]oxepin-10-yl)-4-methylpiperazine or a pharmaceutically acceptable salt thereof, and from about 67 to about 94% by weight of an inert pharmaceutical carrier; and a duodenal soluble coating having from about 7 to about 15% by weight of said core of hydroxypropyl methylcellulose phthalate as a duodenal-soluble coating, said coating having a thickness of from about 0.1 mm to about 0.2 mm and dissolving at a pH of from about 5.0 to 5.5.

Still more particularly this invention relates to a duodenal-soluble coated pharmaceutical tablet in dosage unit form comprising from about 10 to about 50 parts by weight of 1-(2-chlorodibenzo[b,f]oxepin-10-yl)-4-methylpiperazine or a pharmaceutically acceptable salt thereof, from about 100 to about 200 parts by weight of an inert pharmaceutical carrier, and from about 10 to about 30 parts by weight of a duodenal-soluble coating of hydroxypropyl methylcellulose phthalate having a thickness of from about 0.1 to 0.2 mm and dissolving at a pH of about 5.0 to 5.5.

DETAILED DESCRIPTION OF THE INVENTION

The compound, 1-(2-chlorodibenzo[b,f]oxepin-10-yl)-4-methylpiperazine, has been found to possess potent anti-psychotic properties, while at the same time having minimal extrapyramidal and cardiovascular liabilities. This compound can be prepared in accordance with the following reaction scheme.

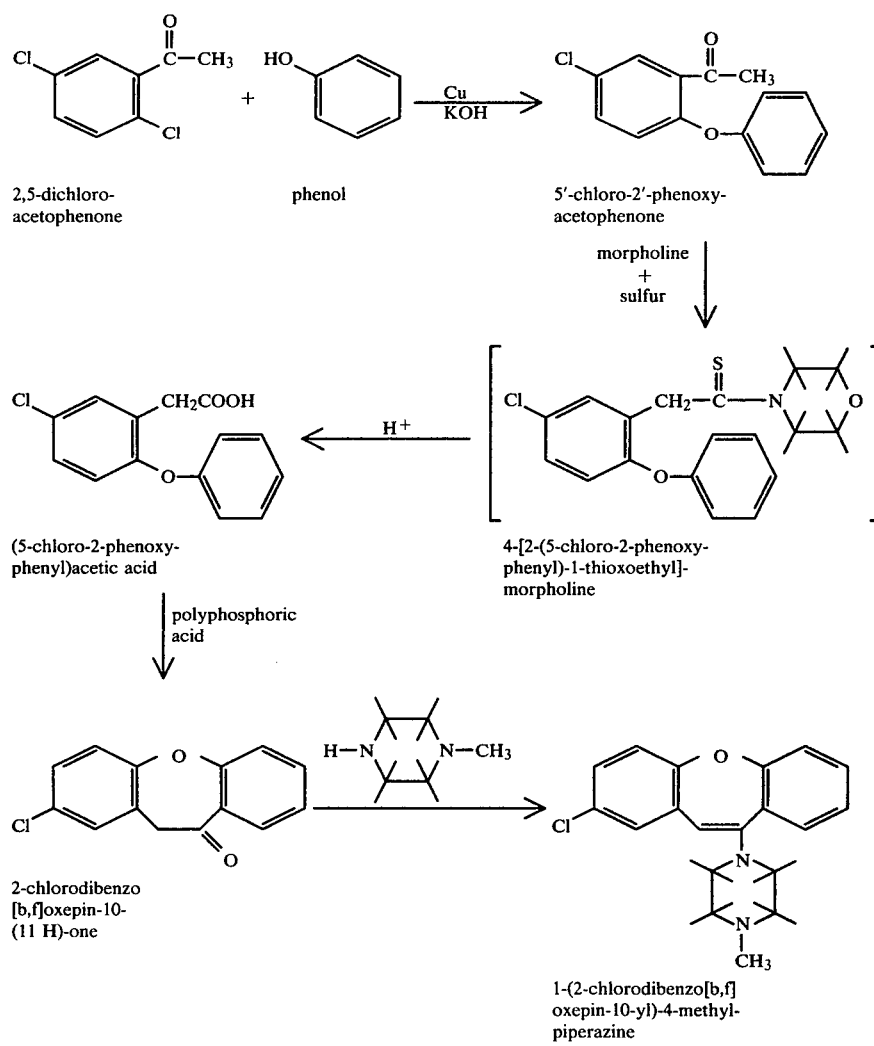

Prior to the present invention, the major difficulty encountered with this remarkable drug has been the somewhat erratic and irregular physiological availability of the drug upon administration, as measured by the absorption of the drug in the bloodstream. It has now been discovered that these unpredictable blood levels heretofore obtained are due to a combination of factors involving both the solubility and the chemical instability of the compound at low pH in aqueous solutions.

In an aqueous solution at a pH of 1.0 the compound 1-(2-chlorodibenzo[b,f]oxepin-10-yl)-4-methylpiperazine is soluble to the extent of 20 mg/ml; at a pH of 3.0 the solubility of this compound is 15 mg/ml; and at a pH of 4.3 the solubility of this compound is 4 mg/ml. Although this compound is more soluble in a 50% methanol-water system, even here at a pH of 7.0 the solubility decreases to 2 mg/ml, whereas the compound is totally insoluble at a pH of 8.0 in a 50% methanol-water system. Thus, it can be seen that the drug has its maximum solubility in aqueous solutions at a low pH and should be ideally dissolved and available for absorption in humans under conditions of gastric acidity, i.e., a pH of 1–5. On the other hand, if the drug is exposed to the relatively alkaline portions of the intestinal tract, i.e., a pH greater than 7.5, the drug remains undissolved and is unavailable for absorption in humans.

However, paradoxically, under the acidic conditions of maximum dissolution and absorption, the drug substance is itself the most labile from a chemical point of view. As previously indicated, the compound belongs to a class of enamines that are readily hydrolyzed under acidic aqueous conditions. Thus, at 25° C. and at a pH of 1.5, the half-life of 1-(2-chlorodibenzo[b,f]oxepin-10-yl)-4-methylpiperazine in a 50% (v/v) methanol-water solution is 0.12 hour, whereas at the same temperature and at a pH of 6.0, the half-life of the compound is increased to 269 hours. Similarly, at the normal body temperature of 37° C. and at a pH of 1.5, the half-life of the compound is 0.12 hour, whereas at the same temperature and at a pH of 6.0, the half-life of the compound is 159 hours. Thus, under normal conditions of gastric acidity, the drug substance undergoes acid degradation with a concomitant loss of therapeutic activity.

The compositions contemplated to be within the scope of the present invention comprise certain pharmaceutical compositions of 1-(2-chlorodibenzo[b,f]oxepin-10-yl)-4-methylpiperazine that have been coated with a controlled amount of a particular duodenal-soluble, film-forming material. The term duodenal-soluble coat as used herein is not necessarily limited to the disruption and dissolution of a film coat or a protective coat in the duodenum. Rather, the term duodenal-soluble is intended to refer to a single coating of hydroxypropyl methylcellulose phthalate having certain properties that enable this coating to be disrupted and/or dissolved under the relatively mild acidic conditions of the duodenum, but not in the normally highly acidic environment of the stomach. Thus, if for some reason the gastric contents of an individual are only mildly acidic or have been partially neutralized, as for example by means of an antacid, the duodenal-soluble coating may actually begin to be disrupted and dissolved in the stomach rather than in the duodenum. More particularly, the term duodenal-soluble coating is intended to refer to a single coating of hydroxypropyl methylcellulose phthalate having a prescribed thickness of from 0.1 to 0.2 mm and which will dissolve at a pH of about 5.0 to 5.5. The term "single" coating refers to a single discrete coating composition, albeit it may have been applied to the drug substance as a series of multiple steps. This term is distinguished from "multiple" coatings which refer to a number of discrete different coating compositions, each of which have a separate function to perform. The term coating thickness refers to the thickness of a single coating layer and does not refer to the increase in tablet thickness due to the application of a single coating.

The coated pharmaceutical compositions contemplated within the scope of this invention comprise essentially duodenal-soluble coated core granules, medicated nonpareils and tablets containing the active ingredient. In the uncoated core compositions the active ingredient is present in a range of from about 6 to about 33% by weight of the uncoated core composition. Alternatively, when present in a finished dosage unit form, such as a 100–300 mg tablet, the amount of active ingredient can range from about 10 to about 50 parts by weight of the coated, finished tablet.

The present invention is not merely limited to the free base of the active ingredient, 1-(2-chlorodibenzo[b,f]oxepin-10-yl)-4-methylpiperazine, but also includes the various pharmaceutically acceptable salts of the active ingredient. The expression pharmaceutically acceptable salts refers to any non-toxic organic or inorganic acid addition salts of the base compounds. Such salts can exist in either a hydrated or substantially anhydrous form.

Illustrative inorganic acids which form suitable salts include hydrochloric, hydrobromic, sulfuric and phosphoric acids as well as acid metal salts such as sodium monohydrogen orthophosphate and potassium hydrogen sulfate. Illustrative organic acids which form suitable salts include the mono, di and tricarboxylic acids. Illustrative of such acids are, for example, acetic, propionic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methanesulfonic acid and 2-hydroxyethanesulfonic acid. The pharmaceutically acceptable salt preferably employed is the maleate salt.

The concept of using a film-forming material as an enteric coating to protect acid labile drugs is well known. Under idealized dissolution conditions the drug in such enteric coated compositions is not released in the highly acidic environment of the stomach but is released in the alkaline environment of the lower gastro-intestinal tract. Generally, the form in which a drug is most readily absorbed from the intestinal tract is as the non-ionized species. In the case of the compound 1-(2-chlorodibenzo[b,f]oxepin-10-yl)-4-methylpiperazine, the non-ionized species exhibits such a low solubility in the intestinal tract that it hinders the disintegration and dispersion of the drug substance from its dosage form, thereby preventing subsequent solution and absorption from occurring.

Paradoxically, the maximum solubility and maximum dissolution of this particular drug occurs at a low acid pH—precisely under conditions of its maximum chemical instability! Thus, it is essential that the drug be protected from the high acidity of the gastric contents in order to prevent acid degradation from occurring, and yet be available for solubilization and subsequent absorption under relatively mild acid conditions, such as are present in the duodenum, before reaching the alkaline conditions of the intestinal tract in which the drug is insoluble and unabsorbed. Whereas the enteric coatings of the prior art serve to protect such drugs from acid degradation, these coatings are removed only under alkaline conditiions, i.e., at a pH greater than 7.5, at which point this particular drug substance is insoluble and unavailable for absorption. Thus, the desired film-forming substance should be insoluble in strongly acidic pH conditions of from 1 to 5 as found in the stomach, and be soluble under the slightly acidic pH conditions of from 5 to 7 found in the duodenum. Preferably, it is desired that the film-forming substance dissolve at a pH of from 5.0 to 5.5.

Additionally, the film-forming material should be capable of producing a strong, continuous film that results in smooth and elegant coatings. The resulting duodenal-soluble coating should be stable to heat, light, moisture and air; it should be non-toxic, inert and have no taste, color or odor. Finally, the ideal duodenal-soluble coating must resist cracking and chipping on impact.

I have discovered that certain esters of hydroxypropyl methylcellulose and phthalic anhydride, when applied as a single coating having a thickness of from 0.1 to 0.2 mm, satisfy these requirements, and are particularly useful as duodenal-soluble coatings for compositions containing 1-(2-chlorodibenzo[b,f]oxepin-10-yl)-4-methylpiperazine. These duodenal coatings are characterized by having a free phthalic acid content of less than 1%, a methoxyl content of from 18 to 25%, a hydroxypropoxyl content of from 4 to 10% and a carboxybenzoyl content of from 20 to 35%. The viscosity of a 15% solution of these coatings in 50% methylene chloride-methanol (w/w) at 20° C. ranges from 190 to 240 cps ±20%.

Coatings prepared from these materials are characterized by the fact that they remain intact and are substantially insoluble in aqueous solutions having a pH of less than 5.0, but are readily disrupted and dissolved in aqueous solutions having a pH of about 5.0 to 5.5. Thus, pharmaceutical compositions containing 1-(2-chlorodibenzo[b,f]oxepin-10-yl)-4-methylpiperazine, coated with such duodenal-soluble hydroxypropyl methylcellulose phthalate coatings, are protected against acid decomposition of the active ingredients while in contact with normal gastric contents under normal residence conditions. However, upon passage through the pylorus into the duodenum, where the gastric contents are normally neutralized to a pH of from about 4 to about 7, the duodenal-soluble coating of such compositions is disrupted and dissolved, releasing the drug substance and enabling it to be solubilized and absorbed into the bloodstream.

The amount of hydroxypropyl methylcellulose phthalate present in coated granules, medicated nonpareils or tablets varies from 7 to about 15% by weight of the total composition thereby providing a film of sufficient thickness as to be crack resistant. In a finished duodenal-soluble coated pharmaceutical tablet suitable for oral ingestion an amount of from about 10 to about 30 parts by weight of hydroxypropyl methylcellulose phthalate is effectively employed.

In addition to the required amount of hydroxypropyl methylcellulose phthalate, the thickness of the finished coat is deemed critical due to the peculiar solubility and acid instability characteristics of this particular drug substance. Thus, too thin a tablet coating results in the crazing, chipping and peeling of the coatings with normal handling. More importantly, however, coatings that are too thin rupture and dissolve prematurely, releasing their core contents in the stomach wherein the active drug substance is subject to acid degradation.

Inasmuch as the release of the drug substance is also a function of the coating thickness, a coating that is too thick results in a delayed release of the drug substance. Once the drug has passed through the duodenum and into the relatively alkaline portion of the upper and lower intestinal tract, it remains essentially insoluble and unabsorbed.

In order that the dissolution of this particular drug substance occurs at the appropriate time, I have discovered that a coating thickness of from about 0.1 to 0.2 mm is required. Preferably a coating thickness of 0.1 to 0.15 mm is employed. As seen in Example 10 below, a coating thickness of less than about 0.1 mm is unsatisfactory in that the coating is too thin to protect the drug substance from disintegration and acid degradation by the gastric fluid. Conversely, a coating thickness greater than about 0.2 mm is also unsatisfactory in that no dissolution of the drug substance occurs in the simulated duodenal fluid. Dissolution of the drug substance occurs only in the simulated intestinal fluid, at which pH the drug is relatively insoluble.

The term inert pharmaceutical carrier as used herein is intended to encompass those ingredients which in and of themselves are pharmacologically inactive, and which are generally employed in the art of granulating and tableting. These pharmaceutical excipients include diluents, such as starch, microcrystalline cellulose, calcium phosphate, calcium sulfate, lactose, kaolin, mannitol, crystaline sorbitol or powdered sugar, which generally serve to increase tablet bulk and render the pharmaceutical composition more suitable for compression.

Additionally, a binder is also generally employed to impart a cohesiveness to the formulation and in the case of tablets to insure tablet integrity following compression. Materials commonly employed in this capacity include starch, gelatin, sucrose, glucose, dextrose, molasses, microcrystalline cellulose and natural or synthetic gums such as acacia, sodium alginate, carboxymethylcellulose, and polyvinylpyrrolidone.

The term pharmaceutical carrier as used herein also includes lubricants that are added to improve the flow of tablet granulations and prevent adhesion of tablet material on the surface of tablet dies and punches. Lubricants that can be favorably employed in the present invention include talc, hydrogenated vegetable oils, stearic acid and salts of stearic acid, as for example, calcium stearate, magnesium stearate, aluminum stearate and zinc stearate.

Also included within the scope of the term inert pharmaceutical carriers are disintegrating agents that are added to a pharmaceutical composition in order to assist in the break-up and disintegration of the composition following administration. Disintegrating agents that are advantageously employed include starch, and starch derivatives such as specially modified cold water starches and carboxymethylated starches. Natural and synthetic gums such as locust bean, karaya, guar, tragacanth and agar can also be employed as disintegrants because of their well-known capacity to swell in water. In some cases, surfactants can also be included to enhance dissolution.

The term inert pharmaceutical carrier is also intended to include any pharmaceutically acceptable flavoring agents that are added to enhance the aesthetic qualities of the pharmaceutical composition and make it more acceptable to the patient.

The core granules, medicated nonpareils or core tablets employed herein are prepared in the usual manner using methods well-known to those versed in the art. Granulations are prepared using either a wet or dry granulation process. In the wet granulation method the active ingredient, inert diluents and disintegrating agents are blended together to form a fine powder blend. To provide for more uniform solubilization and absorption the active ingredient may be milled prior to formulation so as to provide a particle size distribution of less than 150 microns in diameter. Preferably, the compound is milled with a portion of a pharmaceutical carrier, such as lactose, to obtain a particle size of from 1 to 25 microns in diameter. Solutions of a binding agent are added to the powder blend with stirring until the entire powder mass has a damp consistency. The mixture is forced through a 6- or 8-mesh screen to provide wet granulations, which are placed in shallow trays and dried to the proper moisture consistency. After drying, the granulations are further reduced in particle size by passing through a 12- to 20-mesh screen, depending upon the diameter of the tablet punch to be employed.

Alternatively, dry granules suitable for coating or compression into tablets can be prepared by blending a mixture of the milled or unmilled active ingredient, the various inert pharmaceutical carriers to be employed and a portion of the lubricant. The resulting powdered mixture is compressed into large tablets or slugs which are then comminuted through a suitable mesh screen to obtain the desired size granules as a dry granulation.

The resulting granules, whether obtained by a wet or dry granulation method, are coated with the film-forming material described above and incorporated as duodenal-soluble coated granules in suitable dosage forms such as capsules, tablets or suspensions. The film-coated granules can be blended with the remaining lubricant and compressed directly into tablets of film-coated granules. Preferably, uncoated granules are blended with the remaining lubricant and compressed into core tablets, said core tablets being film coated.

The basic mechanical unit involved in tablet compression involves the operation of two steel punches within a steel die cavity. The tablet is formed by the pressure exerted on the granulation via the punches within the die cavity. The core tablets so formed are coated with the film-forming material to prepare duodenal-soluble coated tablets in dosage unit form suitable for oral ingestion. Alternatively, non-pareil seed cores can be moistened and dusted with the active ingredient. These medicated non-pareil seed cores can then be coated with the film-forming material and encapsulated in hard or soft gelatin capsules to prepare duodenal-soluble medicated non-pareils in a convenient dosage unit form.

In general, the tablets or granulations are coated by dissolving the hydroxypropyl methylcellulose phthalate film-forming material in a suitable organic solvent to form approximately a 2 to 10% solution (w/v). Suitable organic solvents include those which convey the film-forming material uniformly to the coating surface, and which will rapidly dry without causing "orange-peel" coats. Solvent toxicity, flammability and cost are additional factors to be considered. Solvents that may be successfully employed, either alone or in combination, include methanol, ethanol, isopropanol, chloroform, acetone, methyl ethyl ketone and methylene chloride. A particularly useful solent combination for the hydroxypropyl methylcellulose phthalate film-forming material is a 50% ethanol-methylene chloride solution (w/w).

The coating solution is applied to the drug containing cores using any of the conventional methods of application, i.e., spraying ladling or dip coating. Preferably, the cores to be coated are placed in a conventional, rotating coating pan and the organic solvent coating solution is sprayed onto the cores by means of a spray gun or other suitable atomizing equipment. Additional applications of coating solution are made at frequent intervals and dried with warm air until the desired coating thickness is obtained. At the completion of the coating process the coated dosage unit is spread on racks for oven drying for an aging or curing period so that the final characteristics of the film are realized.

Additional ingredients may be added to the film-forming solution such as plasticizers, lubricants, surfactants and flavoring agents. Plasticizers such as glycerin, propylene glycol, castor oil and low molecular weight polyethylene glycols are useful in preserving and improving the film-forming ability, film strength, flexibility and tack resistance of the coating. Surfactants can also be added to improve the spreading properties of the film-coating solution or as an aid in dissolving the duodenal-soluble coat upon ingestion. Natural or synthetic flavors or sweeteners, either in powdered or liquid form, can also be added to the film-forming solution to improve the palatability of the duodenal-soluble coated compositions and to enhance patient compliance.

In accordance with the present invention, I have discovered that a tablet core comprising from about 10 to about 50 parts by weight of 1-(2-chlorodibenzo[b,f]oxepin-10-yl)-4-methylpiperazine or a pharmaceutically acceptable salt thereof, and containing from about 100 to about 200 parts by weight of an inert pharmaceutical carrier when coated with from about 10 to about 30 parts by weight of the uncoated tablet core with a hydroxypropyl methylcellulose phthalate coating having a thickness of from about 0.1 to 0.2 mm and dissolving at a pH of from about 5.0 to 5.5, provides a particularly convenient dosage unit form that is therapeutically effective. That is to say, such coated tablets suitably protect the compound 1-(2-chlorodibenzo[b,f]oxepin-10-yl)-4-methylpiperazine from acid degradation in the stomach. However, the coating is not of such a nature as to release the active ingredient in the more alkaline portion of the gastro-intentinal tract where the drug substance would remain insoluble and unavailable for absorption. Rather, the duodenal-soluble coatings of the present invention are designed to disrupt and dissolve at a pH of about 5.0 to 5.5, thereby releasing the active ingredient in the slightly acidic region of the duodenum, a region in which the compound remains sufficiently stable and yet sufficiently soluble so as to be subsequently absorbed into the bloodstream.

Thus, under simulated in vitro conditions, duodenal-soluble coated tablets prepared in accordance with the present invention remain essentially unchanged after 1 hour in simulated gastric fluid, whereas at a pH of 5.0 in simulated duodenal fluid, disintegration occurs in from 11 to 50 minutes, depending upon the thickness of the coating. Moreover, under simulated in vivo conditions in dogs, administration of an uncoated aqueous suspension of the drug results in no apparent absorption of the drug in the bloodstream of the animal due to acid degradation, whereas a duodenal-soluble coated tablet administered to these same animals permits the drug to be absorbed and to provide sustained plasma levels of therapeutic efficacy.

The following specific examples more particularly describe my invention, but are not to be construed as limiting the scope thereof.

EXAMPLE 1

5'-Chloro-2'-phenoxyacetophenone

To a stirred solution of 52 grams of 85% potassium hydroxide dissolved in 250 ml of ethanol is added 73 grams of phenol. The solution is stirred for 15 minutes and the solvent removed by distillation. To the remaining residue is added 73 grams of phenol, 116 grams of 2,5-dichloroacetophenone and 10.5 grams of copper powder. The resulting mixture is refluxed for 5 hours with stirring, cooled, treated with a 2 N solution of sodium hydroxide and extracted with ethyl ether. The combined ether extracts are washed with water until the water wash appears neutral, then dried over anhydrous sodium sulfate and filtered to remove the dehydrating agent. The solvent is removed from the filtrate by distillation and the residue is vacuum distilled to obtain 55 grams of 2-phenoxy-5-chloroacetophenone having a b.p. of 126°–130° C. and 0.005 mm Hg. Upon recrystallization from ethanol, the compound has an m.p. of 56°–58° C.

EXAMPLE 2

(5-Chloro-2-phenoxyphenyl)acetic acid

Fifty grams of 5′-chloro-2′-phenoxyacetophenone, prepared in accordance with the procedure of Example 1, 27.5 ml of morpholine and 11.5 grams of precipitated sulfur are refluxed for a period of 9 hours. The resulting mixture is cooled and dissolved in benzene. The benzene solution is extracted three times with a 2 N solution of hydrochloric acid, washed with water, extracted three times with a 3 N solution of sodium hydroxide, washed with water until the water washings are neutral, dried over anhydrous sodium sulfate and filtered to remove the dehydrating agent. The dried organic solvents are removed from the filtrate by distillation leaving a residue of 69 grams of crude 4-[2-(5-chloro-2-phenoxyphenyl)-1-thioxoethyl]morpholine.

To this morpholine residue is added 290 ml of glacial acetic acid, 61 ml of water and 87 ml of sulfuric acid (96%), and the mixture refluxed for a period of 21 hours. On cooling, the reaction mixture is dissolved in ethyl ether, washed with water until the water wash appears neutral and extracted with a 10% sodium carbonate solution. The aqueous alkaline layer is acidified with a 2 N solution of hydrochloric acid and re-extracted into diethyl ether. The ether solution is washed with water until the water washings are neutral, dried over anhydrous sodium sulfate and filtered. The solvent is removed by distillation from the filtrate and the remaining residue is crystallized from cyclohexane to yield 30.5 grams of (5-chloro-2-phenoxyphenyl)acetic acid having a m.p. of 119°–123° C.

EXAMPLE 3

2-Chlorodibenzo[b,f]oxepin-10(11H)-one

Polyphosphoric acid, 500 grams, is heated to 120° C. and 30.5 grams of (5-chloro-2-phenoxyphenyl)acetic acid, prepared in accordance with the procedure of Example 2, is slowly added under an atmosphere of nitrogen with stirring. The reaction mixture is maintained at 120° C. for a period of about two hours, poured over a mixture of ice and water, and extracted into ethyl ether. The combined ether extracts are washed with water until the water washings appear neutral, extracted with a 2 N solution of sodium hydroxide, washed again with water until the water washings are neutral, dried over anhydrous sodium sulfate and filtered. The dried organic solvent is removed from the filtrate by distillation and the residue distilled in vacuo to yield 21 grams of 2-chlorodibenzo[b,f]oxepin-10(11H)-one having a b.p. of 127°–134° C./0.005 mm Hg. Upon recrystallization from methanol, a compound is obtained having an m.p. of 75°–76° C.

EXAMPLE 4

1-(2-Chlorodibenzo[b,f]oxepin-10-yl)-4-methylpiperazine

Thirty grams of 2-chlorodibenzo[b,f]oxepin-10(11H)-one, prepared in accordance with the procedure of Example 3, 45 grams of N-methylpiperazine and a solution of 8 grams of p-toluenesulfonic acid monohydrate in 150 ml of xylene are refluxed for a period of 22 hours in a reflux apparatus equipped with a Dean-Stark trap in order to remove the water that forms. The reaction mixture is cooled, treated with a solution of sodium bicarbonate, washed with water until the water washings are neutral, dried over anhydrous sodium sulfate and filtered through a column of neutral aluminum oxide. The filtrate is concentrated to dryness in vacuo and the residue, 46 grams, crystallized from ethanol to yield 32 grams of 1-(2-chlorodibenzo[b,f]oxepin-10-yl)-4-methylpiperazine having an m.p. of 119°–121° C.

EXAMPLE 5

Preparation of a Duodenal-Soluble Coated Tablet

A duodenal-soluble coated pharmaceutical tablet suitable for oral ingestion is prepared as follows:

|     |                                                    | Grams |
| --- | -------------------------------------------------- | ----- |
| (a) | 1-(2-chlorodibenzo[b,f]oxepin-10-yl)-4-methylpiperazine | 15    |
| (b) | Lactose                                            | 81    |
| (c) | Corn starch                                        | 31.2  |
| (d) | Instant corn starch                                | 4.3   |
| (e) | Microcrystalline cellulose                         | 21.5  |
| (f) | Carboxymethylated starch                           | 6     |
| (g) | Magnesium stearate                                 | 1     |
| (h) | Hydroxypropyl methylcellulose phthalate            | 20    |
| (i) | Ethyl alcohol                                      | 250   |
| (j) | Methylene chloride                                 | 250   |

The 1-(2-chlorodibenzo[b,f]oxepin-10-yl)-4-methylpiperazine, lactose, corn starch, instant corn starch and microcrystalline cellulose are blended, passed through a No. 20 mesh screen, and reblended. A wet granulation is prepared by the addition of 61 ml of water, dried, and passed through a No. 12 mesh screen. The granulation so obtained is lubricated with the carboxymethylated starch and magnesium stearate and compressed into approximately 1000 core tablets weighing 200 mg each.

Hydroxypropyl methylcellulose phthalate, having a free phthalic acid content of less than 1%, a methoxyl content of 20 to 25% , a hydroxypropyl content of 5 to 10%, a carboxybenzoyl content of 20 to 24%, a viscosity of 240 cps±20% (at 20° C. in a 15% solution of methylene chloride/methanol mixture of equal weight), and which will dissolve in an aqueous solution at a pH of 5.0, is added to the ethyl alcohol and methylene chloride to form a 4% solution. The resulting solution is sprayed onto 1000 core tablets rotating in a coating pan. The coated tablets are rotated under a current of warm air (37° C.) until dry and tack-free. Each coated tablet weighs approximately 220 mg and contains 20 mg of duodenal coating having a coating thickness of approximately 0.14 mm.

Alternatively, the granules prepared above can be spray-coated to provide duodenal-soluble coated granules containing the active ingredient. These duodenal-soluble coated granules can be filled into 1000 hard shell gelatin capsules to provide a suitable dosage unit in capsule form.

EXAMPLE 6

Preparation of Capsules Containing Duodenal-Soluble Coated Non-Pareil Seeds

A capsule containing duodenal-soluble coated non-pareil seeds suitable for oral ingestion can be prepared as follows:

| | | Grams |
|---|---|---|
| (a) | 1-(2-chlorodibenzo[b,f]oxepin-10-yl)-4-methylpiperazine | 50 |
| (b) | Precipitated calcium carbonate, U.S.P. Heavy | 100 |
| (c) | Non-pareil seeds (16–18 mesh) | 100 |
| (d) | Polyvinylpyrrolidone | 20 |
| (e) | Magnesium stearate | 2 |
| (f) | Hydroxypropyl methylcellulose phthalate | 20 |
| (g) | Ethyl alcohol | 250 |
| (h) | Methylene chloride | 250 |

The 1-(2-chlorodibenzo[b,f]oxepin-10-yl)-4-methylpiperazine and calcium carbonate are blended and screened through a No. 30 mesh screen in order to obtain a fine homogenous powder. The non-pareil seeds are placed in a rotating coating pan and a portion (approximately 10%) of a 10% solution of polyvinylpyrrolidone in ethanol is sprayed onto the rotating non-pareil seeds to dampen them. Approximately 8–12% of the powder mix is dusted onto the dampened seeds. The rotation of the coating pan is continued until the powder is evenly distributed and adhered to the seeds and the solvent evaporated. The seeds are again wet with a similar portion of the polyvinylpyrrolidone solution, again dusted with the powder mixture, rotated and dried. This process is continued until all of the powder misture containing the active ingredient is evenly dusted onto the non-pareil seeds.

A 4% solution of hydroxypropyl methylcellulose phthalate is prepared by dissolving in the ethyl alcohol and methylene chloride. The particular hydroxypropyl methylcellulose phthalate employed has a free phthalic acid content of less than 1%, a methoxyl content of 18 to 22%, a hydroxypropyl content of 4 to 9%, a carboxybenzoyl content of 27 to 35%, a viscosity of 190 cps±20% (at 20° C. in a 15% solution of methylene chloride/methanol mixture of even weight), and dissolves in an aqueous solution at a pH of 5.5. The non-pareil seeds which have been coated with the active ingredient are rotated in a coating pan and sprayed with the hydroxypropyl metylcellulose phthalate solution. The duodenal-soluble coated non-pareil seeds are dried, lubricated by dusting with magnesium stearate and filled into approximately 1000 hard shell gelatin capsules. Each capsule weighs approximately 300 mg and contains 50 mg of the active ingredient.

EXAMPLE 7

In Vitro Disintegration of Duodenal-Soluble Coated Tablets in Simulated Gastric Fluid The following illustrates the in vitro dissolution of the duodenal-soluble coated (DSC) tablets of the present invention in the critical pH range of from 4 to 7. This pH range is the range in which the compound, 1-(2-chlorodibenzo[b,f]oxepin-10-yl)-4-methylpiperazine, remains sufficiently acid-stable and yet is sufficiently water-soluble so as to biologically absorbed.

Thirty duodenal-soluble coated placebo tablets each prepared essentially in accordance with the procedure of Example 5, are placed in a small, baffled coating pan and sprayed with a 4% (w/v) solution of hydroxypropyl methylcellulose phthalate in methylene chloride and ethyl alcohol (1:1) to the designated weight. One group of tablets is spray coated with a hydroxypropyl methylcellulose phthalate having the characteristics described in Example 5, and is designated in Table I by the pH of an aqueous solution in which the coating will dissolve (pH=5.0). The remaining group of tablets is spray coated with a hydroxypropyl methylcellulose phthalate having the characteristics described in Example 6 and is designated in Table I by the pH of an aqueous solution in which the coating will dissolve (pH=5.5). The dissolution time of the tablets is determined in accordance with the standard procedure set forth in the United States Pharmacopeia, Vol XIX, pp 651 (1975), using a USP rotating basket assembly at a speed of 100 rpm and a temperature of 37° C.

All of the tablets are first run in Simulated Gastric Fluid (no enzymes) for a period of 60 minutes, removed, drained dry on absorbent material and the duodenal-soluble coat visually examined for evidence of deterioration. The tablets are then transferred to the appropriate citrate buffered solution and the disintegration time determined by the appearance of particles in the buffer solution. All buffer solutions are prepared by dissolving 10.507 g of citric acid in 950 ml of purified water, adjusting to the desired pH using a 1 N solution of sodium hydroxide, and q.s. to 1000 ml. The data obtained are summarized in Table I below.

TABLE 1

| Hydroxypropyl methylcellulose phthalate | Weight DSC* Per Tablet(mg) | DSC* Film Coat Thickness(mm) | Condition of DSC* After 1 Hour in Simulated Gastric Fluid | pH of Buffer Solution | Disintegration Time in Buffer Solution (minutes) |
|---|---|---|---|---|---|
| pH 5.0 | 22 | 0.16 | unchanged | 4.5 | >60 |
| | " | " | " | 5.0 | 18 |
| | | | | 5.5 | 11 |
| | 26 | 0.19 | unchanged | 4.5 | >60 |
| | " | " | " | 5.0 | 32 |
| | " | " | " | 5.5 | 15 |
| | 32 | 0.20 | unchanged | 4.5 | >60 |
| | " | " | " | 5.0 | 39 |
| | " | " | " | 5.5 | 17 |
| pH 5.5 | 12 | 0.09 | intact-some deterioration | 4.5 | 13 |
| | " | " | " | 5.0 | 5 |
| | " | " | " | 5.5 | 3 |
| | 20 | 0.14 | unchanged | 4.5 | >60 |
| | " | " | " | 5.0 | >60 |
| | " | " | " | 5.5 | 22 |
| | 20 | 0.14 | unchanged | 6.0 | 11 |

TABLE 1-continued

| Hydroxypropyl methylcellulose phthalate | Weight DSC* Per Tablet(mg) | DSC* Film Coat Thickness(mm) | Condition of DSC* After 1 Hour in Simulated Gastric Fluid | pH of Buffer Solution | Disintegration Time in Buffer Solution (minutes) |
|---|---|---|---|---|---|
| " | " | " | " | 6.5 | 8 |
| " | " | " | " | 7.0 | 8 |

*DSC - Duodenal-Soluble Coat

As can be seen, the duodenal-soluble coated tablets remain essentially protected under simulated conditions of gastric acidity, whereas under the slightly acidic conditions encountered in the duodenum, the duodenal-soluble coating is disrupted and dissolved.

EXAMPLE 8

In Vivo Administration of Duodenal-Soluble Coated Tablets

The following Example demonstrates the bioavailability of 1-(2-chlorodibenzo[b,f]oxepin-10-yl)-4-methylpiperazine when administered as a duodenal-soluble coated tablet composition as compared to that of an aqueous suspension. To approximate the gastric acidity of normal human levels, male beagle dogs are pretreated by subcutaneously administering a saline solution of histamine diphosphate (10 mg/ml) at a dose of 0.327 mg/kg in order to induce gastric acid secretion.

In a crossover study each dog receives 1-(2-chlorodibenzo[b,f]oxepin-10-yl)-4-methylpiperazine as the free base, at an oral dose of 20 mg/kg, in the form of a duodenal-soluble coated tablet and as an aqueous suspension. The duodenal-soluble coated tablets are essentially prepared in accordance with the procedure of Example 5. The uncoated suspension is prepared by adding the individual dose to 20 ml of 0.5% methocel solution. All of the dogs are fasted for 16 hours prior to the drawing of their first blood sample. Blood samples are drawn at pre-dose, 0.5, 1.0, 1.5, 2.0 hours and hourly thereafter for a period of 8.0 hours. The blood plasma is separated and quantitatively analyzed for 1-(2-chlorodibenzo[b,f]oxepin-10-yl)-4-methylpiperazine via gas chromatography. The data obtained are summarized in Table II below.

TABLE II

PLASMA LEVELS WITH METHOCEL SUSPENSION VS. DUODENAL-SOLUBLE COATED TABLET AT DOSE OF 20 mg/kg IN MALE BEAGLE DOGS WITH HISTAMINE STIMULATED STOMACH ACID SECRETION

| | Concentration (ng/ml of plasma) | | | | | | | |
|---|---|---|---|---|---|---|---|---|
| | Suspension Dose | | | | Tablet Dose | | | |
| Time (hours) | Dog 1 | Dog 2 | Dog 3 | Dog 4 | Dog 1 | Dog 2 | Dog 3 | Dog 4 |
| Predose | *— | — | — | — | — | — | — | — |
| 0.5 | — | — | trace | 7 | — | — | — | — |
| 1.0 | 11 | — | — | trace | — | — | — | — |
| 1.5 | 14 | — | trace | trace | — | — | — | — |
| 2.0 | trace | — | trace | — | — | — | — | — |
| 3.0 | 10 | — | — | trace | 11 | — | 123 | 33 |
| 4.0 | 9 | — | — | — | 20 | 139 | 84 | 39 |
| 5.0 | trace | — | — | — | 23 | 107 | 73 | 54 |
| 6.0 | trace | — | — | — | 12 | 95 | 86 | 54 |
| 7.0 | — | — | — | — | 32 | 110 | 82 | 44 |
| 8.0 | — | — | — | — | 17 | 80 | 77 | 39 |

*No detectable levels of 1-(2-chlorodibenzo[b,f]oxepin-10-yl)-4-methylpiperazine found in plasma.

As indicated above, dogs in which gastric acid secretion is stimulated prior to oral dosing with a methocel suspension of 1-(2-chlorodibenzo[b,f]oxepin-10-yl)-4-methylpiperazine, develop very low plasma levels of the compound, the maximum being 14 ng/ml. This is due to the chemical instability of the unprotected compound under acidic conditions.

On the other hand dogs in which gastric acid secretion is stimulated prior to oral dosing with a duodenal-soluble coated tablet (20 ng/kg) containing 1-(2-chlorodibenzo[b,f]oxepin-10-yl)-4-methylpiperazine, develop sustained plasma levels of the compound with a maximum observed peak level of 139 ng/ml. This clearly demonstrates the protective action of the duodenal-soluble coating on the drug coat from acidic conditions of the stomach, while at the same time permitting sufficient solubility of the compound under the relatively acidic conditions of the duodenum to enable subsequent absorption to take place. Moreover, the 2 to 3 hour delay in blood level obtained with the duodenal-soluble coated tablet is a further indication that solubilization and subsequent absorption has taken place once the tablet has passed through the stomach.

EXAMPLE 9

The following Example illustrates the importance of applying hydroxypropyl methylcellulose phthalate coatings to 1-(2-chlorodibenzo[b,f]oxepin-10-yl)-4-methylpiperazine via a non-aqueous solvent.

Approximately 15,000 core tablets having the following composition are prepared essentially in accordance with the procedure set forth in Example 5 above.

| Ingredients | Amount (gms) | Amt/Tablet (mgs) |
|---|---|---|
| 1-(2-chlorodibenzo[b,f]oxepin-10-yl)-4-methyl-piperazine | 150 | 10.0 |
| Lactose | 1290 | 86.0 |
| Corn Starch | 466.5 | 31.1 |
| Instant corn starch | 64.5 | 4.3 |
| Microcrystalline cellulose | 324 | 21.6 |
| Carboxymethylated starch | 90 | 6.0 |
| Magnesium stearate | 15 | 1.0 |
| | 2,400 gms | 160.0 mgs |

The 1-(2-chlorodibenzo[b,f]oxepin-10-yl)-4-methylpiperazine, lactose, corn starch, instant corn starch and microcrystalline cellulose are blended, passed through a No. 20 mesh screen and reblended. A wet granulation is prepared by the addition of 900 ml of water, dried and passed through a No. 12 mesh screen. The resulting granulation is lubricated with the carboxymethylated starch and magnesium stearate and compressed into approximately 15.000 core tablets weighing 160 mg each.

An aqueous coating solution is prepared by dissolving 19.5 g of sodium carbonate in 2640 ml of purified water and adding 300 g of hydroxypropyl methylcellulose phthalate with stirring thereto. The mixture is allowed to stand overnight and an additional 6.7 g of sodium carbonate added with stirring. Approximately 4,400 core tablets are placed in a coating pan and coated with this aqueous coating solution until the tablets have an average coat weight of 14 mg/tablet or a coating thickness of about 0.10 mm.

Approximately 100 of the aqueous coated tablets so prepared are treated with hydrogen chloride gas to convert the water soluble coating to the water-insoluble acid form by placing the tablets in a tube and allowing the gas to flow freely through the tube for a period of 15 minutes. The aqueous coated, hydrogen chloride gas treated tablets are washed in purified water until the washings are neutral and dried for 3 hours at 60° C.

An additional 100 of the aqueous coated tablets prepared above are treated with 100 ml of a stirred aqueous solution of 4 N hydrochloric acid for a period of 30 minutes. The tablets are washed in purified water until neutral and dried for 3 hours at 60° C.

An organic coating solution is prepared by dispersing 120 g of the same lot of hydroxypropyl methylcellulose phthalate used in preparing the aqueous coatings above in 1500 ml of methylene chloride. Ethyl alcohol, 1500 ml is added and the mixture stirred for 1–2 hours until solution is effected. Approximately 4,400 core tablets are placed in a coating pan and coated with the organic solvent coating solution until each of the tablets has an average coat weight of 14 mg/tablet or a coating thickness of 0.10 mm.

Examination of the physical appearance of the finished tablets indicates that the use of aqueous coatings results in the preparation of unacceptable tablets, whereas the use of an organic solvent in applying the same coating material results in the preparation of completely acceptable, pharmaceutically elegant tablets. Moreover, the acid treatment required to convert the water soluble coatings to the water insoluble form results in an acid degradation of the active drug substance, viz, 1-(2-chlorodibenzo[b,f]oxepin-10-yl)-4-methylpiperazine as shown in Table III.

coating pan and are sprayed with a solution of 120 gms of the hydroxypropyl methylcellulose phthalate, as described in Example 5 above, dissolved in a mixture of 1500 ml of methylene chloride and 1500 ml of ethyl alcohol. The tablets are sprayed for 10 seconds and dried for 20 seconds with air at 60° C. This cycle is repeated until each group of tablets have coating thicknesses of approximately 0.05, 0.10, 0.16, 0.20 and 0.25 mm.

In order to determine the extent of dissolution the variously coated tablets are subjected to the following schedule:

(A) One hour in USP Gastric Fluid followed by one hour in Simulated Duodenal Fluid (citrate Buffer pH 5.0), and (B) One hour in USP Gastric Fluid followed by one hour in USP Intestinal Fluid (pH 7.5).

One tablet of each of the variously coated tablets is placed in a standard USP Rotating Basket Dissolution Apparatus containing 900 ml of USP Gastric Fluid or 900 ml of Simulated Duodenal Fluid (citrate Buffer pH 5.0) or 900 ml of USP Intestinal Fluid (pH 7.5). The tablets are rotated (100 rpm) at 37° C. for 1 hour in USP Gastric Fluid. If the coating remains intact, the tablets are removed and run for 1 hour in both Simulated Duodenal Fluid and Intestinal Fluid.

Following the alloted time, 50 ml of fluid is removed, filtered and assayed for drug using a Beckman DB-G Spectrophotometer. The amount of drug in solution is determined by comparative absorbence against a Beer's Law plot previously prepared for each fluid.

As can be seen from Table IV below, tablets having a coating thickness of less than 0.1 mm are unsatisfactory. Such coatings are too thin and the tablets are completely disintegrated in Simulated Gastric Fluid. Conversely, coating thicknesses greater than 0.2 mm

TABLE III

| Coating Treatment | Coat Wt (mg/tablet) | Coating Thickness (mm) | Physical Appearance Finished Tablets | Acid Degradation[b] |
|---|---|---|---|---|
| Aqueous solvent coated; HCl gas treated | 14 | 0.10 | off-white; dull coat; 56% of tablets unacceptable[a] | slight |
| Aqueous solvent coated; 4N HCl treated | 14 | 0.10 | brownish-yellow; dull coat; 22% of tablets unacceptable | extensive |
| Organic solvent coated | 14 | 0.10 | white and shiney coat; all tablets acceptable | none |

[a]Unacceptable tablets are those which have a mottled appearance, discolored and/or possess cracked or ruptured coats.
[b]Qualitatively determined by high pressure liquid chromatography assay specific for acid degradation product.

EXAMPLE 10

The following Example illustrates the criticality of coating thickness to this invention.

Approximately 4,400 core tablets prepared as described in Example 9 are placed in an appropriate size are too thick. Such coatings are not dissolved in Simulated Duodenal Fluid within a reasonable period of time. Dissolution of such coated tablets occurs first in Simulated Intestinal Fluid, at which pH the drug is virtually insoluble and unabsorbed.

TABLE IV

| Sample | Tablet wt[a] (mg/tablet) | Coat wt[b] (mg/tablet) | Coat Thickness(mm)[c] | Duodenal Disintegration Time(mm)[d] | Drug Amount in Duodenal Fluid[e] (mg/900 ml) | Intestinal Disintegration Time(mm)[f] | Drug Amount in Intestinal Fluid[g] |
|---|---|---|---|---|---|---|---|
| Core tablet | 160 | — | — | — | — | — | — |
| 1 | 167 | 7 | 0.04 | N/A[h] | | N/A[h] | |
| 2 | 174 | 14 | 0.10 | 11 | 5.6 | 3.5 | 1.2 |
| 3 | 183 | 23 | 0.16 | 32 | 4.7 | 5 | 1.4 |
| 4 | 192 | 32 | 0.20 | 50 | 3.6 | 8 | 1.4 |

TABLE IV-continued

| Sample | Tablet wt[a] (mg/tablet) | Coat wt[b] (mg/tablet) | Coat Thickness(mm)[c] | Duodenal Disintegration Time(mm)[d] | Drug Amount in Duodenal Fluid[e] (mg/900 ml) | Intestinal Disintegration Time(mm)[f] | Drug Amount in Intestinal Fluid[g] |
|---|---|---|---|---|---|---|---|
| 5 | 202 | 42 | 0.25 | >60 | 0 | 10 | 1.0 |

[a] Average - 20 tablets.
[b] Coated tablet weight minus core tablet weight.
[c] Coated tablet thickness minus core tablet thickness divided by two.
[d] Time required in minutes for the onset of core disintegration in Simulated Duodenal Fluid (Citrate Buffer pH 5.0).
[e] Amount of drug after 1 hour in Simulated Duodenal Fluid.
[f] Time required in minutes for the onset of core disintegration in USP Intestinal Fluid (pH 7.5).
[g] Amount of drug after 1 hour in USP Intestinal Fluid.
[h] Not run further - coating disintegrated in USP Gastric Fluid.

I claim:

1. A coated, duodenal soluble, pharmaceutical composition suitable for oral ingestion comprising a core having from 6 to 33% by weight of 1-(2-chlorodibenzo[b,f]oxepin-10-yl)-4-methylpiperazine or a pharmaceutically acceptable salt thereof, and from 67 to 94% by weight of an inert pharmaceutical carrier; and a duodenal soluble coating having from 7 to 15% by weight of said core of hydroxypropyl methylcellulose phthalate, said coating having a thickness of from 0.1 to 0.2 mm and which dissolves at a pH of about 5.0 to 5.5.

2. A composition according to claim 1 wherein the 1-(2-chlorodibenzo[b,f]oxepin-10-yl)-4-methylpiperazine is present as the maleate salt.

3. A composition according to claim 1 which is in the form of a duodenal-soluble coated tablet.

4. A duodenal-soluble coated pharmaceutical tablet for oral ingestion comprising from about 10 to about 50 parts by weight of 1-(2-chlorodibenzo[b,f]oxepin-10-yl)-4-methylpiperazine or a pharmaceutically acceptable salt thereof, from about 100 to about 200 parts by weight of an inert pharmaceutical carrier, and from about 10 to about 30 parts by weight of a duodenal soluble coating of hydroxypropyl methylcellulose phthalate having a thickness of from 0.1 to 0.2 mm and dissolving at a pH of from 5.0 to 5.5.

5. A tablet according to claim 4 wherein the 1-(2-chlorodibenzo[b,f]oxepin-10-yl)-4-methylpiperazine is present as the maleate salt.

* * * * *